United States Patent [19]

Drauz et al.

[11] Patent Number: 4,524,211
[45] Date of Patent: Jun. 18, 1985

[54] PROCESS FOR THE PRODUCTION OF SUBSTITUTED PHOSPHONIC AND PHOSPHINIC ACIDS AND THIAZOLIDINYL PHOSPHONIC AND PHOSPHINIC ACID ESTER INTERMEDIATES

[75] Inventors: Karlheinz Drauz, Freigericht; Hans G. Koban; Jürgen Martens, both of Alzenau; Werner Schwarze, Frankfurt, all of Fed. Rep. of Germany

[73] Assignee: Degussa Aktiengesellschaft, Frankfurt, Fed. Rep. of Germany

[21] Appl. No.: 552,103

[22] Filed: Nov. 16, 1983

[30] Foreign Application Priority Data

Dec. 11, 1982 [DE] Fed. Rep. of Germany ....... 3245887

[51] Int. Cl.³ .......................... C07F 9/30; C07F 9/38; C07F 9/65
[52] U.S. Cl. ...................... 548/111; 260/502.4 R
[58] Field of Search ................. 548/111; 260/502.4 R

[56] References Cited

U.S. PATENT DOCUMENTS 4,443,609 4/1984 Alink et al. ................... 548/146 X
4,469,686 9/1984 Andrews ...................... 548/111 X

FOREIGN PATENT DOCUMENTS 0033919 8/1981 European Pat. Off. .

OTHER PUBLICATIONS

Kudzin, Synthesis No. 8, 1981, pp. 643–645.

Primary Examiner—Richard L. Raymond
Attorney, Agent, or Firm—Cushman, Darby & Cushman

[57] ABSTRACT

There are prepared 1-amino-2-mercapto-2-methylpropyl phosphonic acid or 1-amino-2-mercapto-2-methylpropyl alkylphosphinic acids of the formula

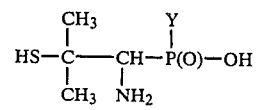

in which Y is hydroxy or an alkyl group by reacting thiazoline-(3) with a phosphonic acid dialkyl ester or an alkylphosphinic acid alkyl ester and then hydrolytically splitting the thiazolidinyl phosphonic acid dialkyl ester or thiazolidinyl alkylphosphinic acid alkyl ester. The thiazolidinyl compounds are new compounds. The 1-amino-2-mercapto-2-methylpropyl phosphonic acid and the 1-amino-2-mercapto-2-methylpropyl alkylphosphinic acids are needed for pharmaceutical purposes.

18 Claims, No Drawings

PROCESS FOR THE PRODUCTION OF SUBSTITUTED PHOSPHONIC AND PHOSPHINIC ACIDS AND THIAZOLIDINYL PHOSPHONIC AND PHOSPHINIC ACID ESTER INTERMEDIATES

BACKGROUND OF THE INVENTION

The invention is directed to a process for the production of 1-amino-2-mercapto-2-methylpropyl phosphonic acid or 1-amino-2-mercapto-2-methylpropyl alkyl phosphinic acids. These compounds are pharmaceutically active materials, especially suitable for the treatment of inflammations, degenerative diseases of the joints such as rheumatoid arthritis and Wilson's illness.

It is known to produce 1-amino-2-mercapto propyl phosphonic and phosphinic acids by reacting thiazolines-(3), in a given case as the hydrochloride, at elevated temperature in the molten condition or in the presence of a solvent with phosphonic acid (phosphorous acid) or a phosphinic acid and subsequently splitting the thiazolidine ring (EPO published application No. 33919, the entire disclosure of which is hereby incorporated by reference and relied upon). The disadvantage of the process especially is that the yields are only about 30%.

SUMMARY OF THE INVENTION

There has now been found a process for the production of 1-amino-2-mercapto-2-methylpropyl phosphonic acid or 1-amino-2-mercapto-2-methylpropyl alkyl phosphinic acids of the formula:

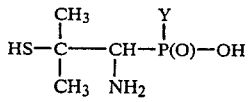

in which Y is a hydroxy or the group $R_1$ where $R_1$ is an alkyl group, e.g. of 1 to 12 carbon atoms, from thiazolines-(3) and phosphorus compounds which is characterized by reacting a thiazoline-(3) of the formula:

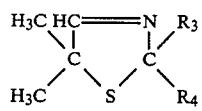

in which $R_3$ and $R_4$ are hydrogen or the same or different alkyl groups or are joined together to form with the carbon atom of the ring a closed alkylene ring with an ester of the formula:

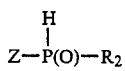

where $R_2$ is an alkoxy group and Z is $R_1$ or $R_2$ and where $R_1$ is an alkyl group as defined above and the ester formed of the formula:

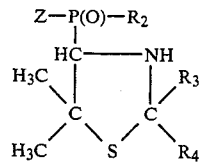

split hydrolytically. This process results in substantially more favorable yields than the known process.

According to the process of the invention there are produced compounds of formula I in which $R_1$ is preferably a branched or unbranched alkyl group of 1 to 12 carbon atoms, especially having 1 to 4 carbon atoms. Compounds which are accessible according to the invention, for example are:
1-amino-2-mercapto-2-methylpropyl phosphonic acid,
1-amino-2-mercapto-2-methylpropyl methylphosphinic acid,
1-amino-2-mercapto-2-methylpropyl ethylphosphinic acid,
1-amino-2-mercapto-2-methylpropyl isopropylphosphinic acid, and
1-amino-2-mercapto-2-methylpropyl butylphosphinic acid.

There are preferably used for the reaction of the invention thiazoline-(3) compounds of the formula (II) in which $R_3$ and $R_4$ are hydrogen or the same or different alkyl groups having 1 to 3 carbon atoms. The alkyl groups can be joined together with the adjacent ring carbon atom to form a closed alkylene ring having 5 to 8 carbon atoms. There can be employed for example thiazoline-(3) compounds such as: 5,5-dimethyl-thiazoline-(3), 2,5,5-trimethyl-thiazoline-(3), 2-ethyl-5,5-dimethyl-thiazoline-(3), 2-propyl-5,5-dimethyl-thiazoline-(3), 2,2-dipropyl-5,5-dimethyl-thiazoline-(3), 2,2-tetramethylene-5,5-dimethyl-thiazoline-(3), 2,2-pentamethylene-5,5-dimethyl-thiazoline-(3) and especially 2-isopropyl-5,5-dimethyl-thiazoline-(3), 2,2-5,5-tetramethyl-thiazoline-(3) and 2,2-diethyl-5,5-dimethyl-thiazoline-(3).

According to the invention the thiazoline-(3) is reacted with an ester of formula (III). In this compound $R_2$ is preferably an alkoxy group which contains a branched or unbranched alkyl group having 1 to 12, especially 1 to 4, carbon atoms. Z stands for $R_1$ or $R_2$ with the above defined meanings. For example there can be employed as esters of formula III dimethyl phosphite, diethyl phosphite, diisopropyl phosphite, dibutyl phosphite, dihexyl phosphite, bis decyl phosphite, bis dodecyl phosphite, methyl ester of methylphosphinic acid, ethyl ester of methyl phosphinic acid, isobutyl ester of methylphosphinic acid, hexyl ester of methylphosphinic acid, dodecyl ester of methylphosphinic acid, isobutyl ester of ethylphosphinic acid, methyl ester of ethylphosphinic acid, methyl ester of propylphosphinic acid, ethyl ester of butylphosphinic acid.

In the reaction according to the invention of the thiazolidine-(3) of formula II with an ester of formula III there are formed esters of formula IV. These esters include for example 5,5-dimethyl-4-thiazolidinyl-phosphonic acid dimethyl ester, 5,5-dimethyl-4-thiazolidinyl-phosphonic acid diethyl ester, 2,5,5-trimethyl-4-thiazolidinyl-phosphonic acid dimethyl ester, 2-ethyl-5,5-dimethyl-4-thiazolidinyl-phosphonic acid diisopropylester, 2-isopropyl-5,5-dimethyl-4-thiazolidinyl-phosphonic acid dimethyl ester, 2-isopropyl-5,5-dimethyl-4- thiazolidinyl-phosphonic acid diethyl ester, 2-isopropyl-5,5-dimethyl-4-thiazolidinyl-phosphonic acid diisopropyl ester, 2,2,5,5-tetramethyl-4-thiazolidinylphosphonic acid diethyl ester, 2,2-diethyl-5,5-dimethyl-4-thiazolidinyl-phosphonic acid diethyl ester, 2,2-tetramethylene-5,5-dimethyl-4-thiazolidinyl-phosphonic acid diethyl ester, 2,2-pentamethylene-5,5-dimethyl-4-thiazolidinyl-phosphonic acid diisopropyl ester, 5,5-dimethyl-4-thiazolidinyl-methylphosphinic acid isobutyl ester, 2-ethyl-5,5-dimethyl-4-thiazolidinyl-ethylphosphinic acid isobutyl ester, 2-isopropyl-5,5-dimethyl-4-thiazolidinyl-methylphosphinic acid methyl ester, 2-isopropyl-5,5-dimethyl-4-thiazolidinyl-methylphosphinic acid isobutyl ester, 2-isopropyl-5,5-dimethyl-4-thiazolidinyl-ethylphosphinic acid isobutyl ester 2,2,5,5-tetramethyl-4-thiazolidinyl-methylphosphinic acid ethyl ester, 2,2-diethyl-5,5-dimethyl-4-thiazolidinyl-methylphosphinic acid methyl ester, 2,2-diethyl-5,5-dimethyl-4-thiazolidinyl-methylphosphinic acid isobutyl ester, 2,2-tetramethylene-5,5-dimethyl-4-thiazolidinyl-ethylphosphinic acid isobutyl ester, and 2,2-pentamethylene-5,5-dimethyl-4-thiazolidinyl-methylphosphinic acid isobutyl ester.

The esters of formula IV are new. They are also a part of the present invention.

To carry out the process of the invention the thiazoline (II) and the ester (III) are employed in substantially any molar ratio. Preferably there are used per mole of ester (III) 0.7 to 1.5 moles, especially about 1.0 mole, of the thiazoline (II). The reaction of the thiazoline (II) with the ester (III) is carried out suitably in liquid medium, preferably in the presence of an inert solvent. As solvent there can be used for example aliphatic or aromatic hydrocarbons which in a given case can be chlorinated. Illustrative are petroleum ether, decane, trichloroethylene, chlorobenzene, benzene, toluene and xylene.

The temperature at which the reaction is carried out in a given case depends on the type of compounds being reacted and, in case a solvent is used, on the type of solvent. Generally it is suitable to choose temperatures near the boiling point of the reaction mixture. In case a solvent is not used, however, the temperature should be at least that at which the reaction mixture is present as a melt. In most cases temperatures of about 50° to 250° C., especially 100° to 190° C. are advantageous.

The pressure can be selected substantially at choice, however, it is generally suitable to carry out the reaction at pressures which do not deviate substantially from normal pressure. In many cases because of the volatility of the materials at the temperatures used, it is necessary to operate at a corresponding elevated pressure.

For the hydrolytic splitting of the ester IV formed in the reaction, this is treated in aqueous medium, namely with at least stoichiometric amounts of water. In the case of the phosphonic acid esters there are required at least 3 moles of water and in the case of the phosphinic acid esters at least 2 moles of water per mole of the ester.

The treatment is carried out with water or with aqueous acids. Suitable are inorganic as well as organic acids insofar as they are not disturbing and especially are not decomposing, for example sulfuric acid or acetic acid. Preferably there is used hydrochloric acid. Generally elevated temperatures are required. Advantageous are temperatures between about 50° C., especially between 80° C., and the boiling point of the medium. The pressure hereby can also be chosen substantially at random. An especially preferred mode of operation is to drive off steam or to lead steam through the reaction mixture.

Unless otherwise indicated all parts and percentages are by weight.

The process can comprise, consist essentially of, or consist of the stated steps with the recited materials.

DETAILED DESCRIPTION

EXAMPLES

A. Production of the Thiazodinyl Phosphonic Acid Esters and the Thiazolidinyl Alkylphosphinic Acid Esters

EXAMPLE 1

A mixture of 314 grams (2 moles) of 2-isopropyl-5,5-dimethyl-thiazoline-(3), 276 grams (2 moles) of diethyl phosphite and 300 ml of petroleum ether (B.P. 120° to 150° C.) were held for 15 hours with the exclusion of moisture at 120° C. and then cooled to 20° C. In the cooling there separated out 2-isopropyl-5,5-dimethyl-4-thiazolidinyl phosphonic acid diethyl ester in the form of colorless crystals. These were filtered off, washed with 1000 ml of petroleum ether (B.P. 30° to 70° C.) and dried at 40° C. and 25 mbar. The yield was 509 grams, corresponding to 86%. The melting point of the material was 68° to 69° C. The elemental analysis showed: C=48.84% (48.79%); H=9.14% (8.87%); N=4.75% (4.74%); P=10.44% (10.49%); S=10.31% (10.85%) - (in parantheses the calculated values for $C_{12}H_{26}NO_3PS$).

EXAMPLE 2

The procedure was as in Example 1 but there were employed 342 grams (2 moles) of 2,2-diethyl-5,5-dimethyl-thiazoline-(3) and the 2,2-diethyl-5,5-dimethyl-4-thiazolidinyl phosphonic acid diethyl ester obtained was dried at 25° C. and 25 mbar. The yield was 489 grams, corresponding to 79%. The melting point of the material was 40° C. The elemental analysis showed: (C=50.29% (50.46%); H=9.31% (9.21%); N=4.51% (4.54%); P=10.20% (10.36%); S=9.98% (10.01%) - (in parantheses the calculated values for $C_{13}H_{28}NO_3PS$).

The spectral analysis showed:
$^1$H-NMR(CDCl$_3$): δ=4.2 (mc. 4H) $0=C\underline{H}_2-CH_3$; 3.20 (d, J=19 Hz, 1H) P-C$\underline{H}$; 3.09 (S, 1H) N$\underline{H}$; 2.1 - 0.7 ppm (m, 22H).

EXAMPLE 3

A mixture of 339 grams (2 moles) of 2,2-tetramethylene-5,5- dimethyl thiazoline-(3), 276 grams (2 moles) of diethyl phosphite and 300 ml of petroleum ether (B.P. 100° to 200° C.) were held for 15 hours at 105° C. Petroleum ether was evaporated from the reaction mixture at 30 mbar until crystallization occurred. The residue was cooled to 0° C. and filtered. The filter residue was washed with 500 ml of cold petroleum ether (B.P. 30° to 70° C.) and dried at 30° C. and 25 mbars. There were obtained 516 grams of 2,2-tetramethylene-5,5-dimethyl-4-thiazolidinyl-phosphonic acid diethyl ester corresponding to a yield of 91%. The melting point of the material was 61° to 63° C. The elemental analysis showed: C=50.77% (50.79%); H=8.60% (8.52%); N - 4.50% (4.56%); P=10.23% (10.08%); S=10.28% (10.43%) - (in parantheses the calculated values for $C_{13}H_{26}NO_3PS$).

The spectral analysis showed:

$^1$H-NMR(CDCl$_3$): δ=4.20 (mc. 4H) O-CH$_2$-CH$_3$; 3.13 (d, J=19 Hz, 1H) P-CH; 2.75 (s, 1H) NH; 2.3 - 1.2 ppm (m, 20H).

EXAMPLE 4

A mixture of 92 grams (0.5 mole) of 2,2-pentamethylene-5,5-dimethyl thiazoline-(3), 69 grams (0.5 mole) of diethyl phosphite and 70 ml of petroleum (B.P. 140° to 200° C.) were held for 15 hours at 125° C. and then cooled to 0° C. In the cooling there separated out crystalline 2,2-pentamethylene-5,5-dimethyl-4-thiazolidinyl phosphonic acid diethyl ester. This material was filtered off, washed with 50 ml of n-pentane and dried for 24 hours at 50° C. and 30 mbar. The yield was 146 grams, corresponding to 91%. The melting point was 77° to 79° C. The elemental analysis showed: C=52.26% (52.32%); (*)
(*)H=8.81(8.78%); N=4.22% (4.36%) - (in parentheses the calculated values for C$_{14}$H$_{28}$NO$_3$(PS).

$^1$H-NMR(CDCl$_3$): δ=4.20 (mc. 4H) O-CH$_2$-CH$_3$; 3.25 (d, J=19 Hz, 1H) P-CH; 2.0 - 1.0 ppm (m, 22H)

EXAMPLE 5

100 grams (0.7 mole) of 2,2,5,5-tetramethylthiazoline-(3) were mixed at 20° C. with 104 grams (0.8 mole) of diethyl phosphite. The mixture was held for 14 hours at 20° C. and 12 hours at 105° C. Then it was distilled. The 2,2,5,5-tetramethyl-4-thiazolidinyl phosphonic acid diethyl ester was obtained as a yellow oil. Its boiling point was 104° to 106° C. at 0.4 mbar. After addition of petroleum ether (B.P. 30° to 70° C.) and cooling there crystallized out of the oil the 2,2,5,5-tetramethyl-4-thiazolidinyl phosphonic acid diethyl ester. The yield was 14.5 grams, corresponding to 75%, based on the thiazoline employed. The elemental analysis of the ester obtained showed: C=46.88% (46.97%); H=8.89% (8.54); N=4.97%
The spectral analysis showed: (4.98%); P=11.11% (11.03%); S=11.40% (11.39%) - in parantheses the calculated values for C$_{11}$H$_{24}$NO$_3$ PS).

EXAMPLE 6

A mixture of 12.6 grams (0.08 mole) of 2-isopropyl-5,5-dimethyl-thiazoline-(3), 10.9 grams (0.08 mole) of methylphosphinic acid isobutyl ester and 15 ml of petroleum (B.P. 140° to 200° C.) were maintained at 120° C. for 15 hours and then cooled to 0° C. In the cooling there separated out 2-isopropyl-5,5-dimethyl-4-thiazolidinyl methylphosphinic acid isobutyl ester. The material was filtered off, washed with 10 ml of cold petroleum ether (B.P. 30° to 70° C.) and dried for 24 hours at 40° C. and 20 mbar. The yield was 18.5 grams, corresponding to 79%. The melting point of the material was 91° to 93° C. The elemental analysis showed: C=53.11% (53.22%); H=9.56% (9.62%); N=4.69% (4.77%); P=10.89% (10.92%); S=10.57% (10.56%) - (in parantheses the calculated value for C$_{13}$H$_{28}$NO$_2$PS).
The spectral analysis showed:

$^1$H-NMR(CDCl$_3$): δ=4.40 (d, J=7 Hz, 1H)-CH; 3.73 (mc, 2H) CH-CH$_2$; 2.80 (d, J=10 Hz, 1H) P-CH; 2.50 (s, sH) NH; 2.24 - 1.40 (m, 11H); 1.15 - 0.07 ppm (m, 6H).

EXAMPLE 7

The procedure was as in Example 6 but there were employed 14.7 grams (0.08 mole) of 2,2-pentamethylene-5,5-dimethyl thiazoline-(3). There were obtained 19.6 grams of 2,2-pentamethylene-5,5-dimethyl-4-thiazolidinyl methylphosphinic acid isobutyl ester, corresponding to a yield of 77%. The melting point of the material was 94° to 96° C. The elemental analysis showed: C=56.41% (56.40%); H=9.66% (9.46%); N=4.36% (4.38%); P=10.06% (10.04%); S=9.76% (9.70%) - (in parantheses the calculated values for C$_{15}$H$_{30}$NO$_2$PS). The spectral analysis showed:

$^1$H-NMR(CDCl$_3$): δ=3.78 (mc, 2H) O-CH$_2$-CH$_3$; 3.12 (d, J=10 Hz, 1H) P-CH; 2.78 (s, 1H) NH; 2.15 - 1.2 (m, 20H); 0.93 ppm (d, J=7 Hz)(CH$_3$)$_2$CH;

B. Hydrolytic Splitting of the Thiazolidinyl-Phosphonic Acid Ester and Thiazolidinyl Alkylphosphinic Acid Ester

EXAMPLE 1

2.95 grams (0.01 mole) of the 2-isopropyl-5,5-dimethyl-4-thiazolidinyl phosphonic acid diethyl ester obtained according to Example A1 was treated with 20 ml of semi-concentrated aqueous hydrochloric acid. The mixture was held under reflux at the boiling temperature for 5 hours, then subjected to a steam distillation and subsequently brought to dryness. The residue was dissolved in 8 ml of water, the solution clarified with activated carbon, mixed with 40 ml of ethanol and regulated to pH of 5 through addition of triethylamine. Thereby there separated out the 1-amino-2-mercapto-2-methylpropylphosphonic acid in the form of colorless crystals. It was filtered off, washed successively with 10 ml of ethanol and 10 ml of dimethyl ether and subsequently dried at 80° C. and 25 mbar. The yield was 1.70 grams, corresponding to 92%. The melting point of the material was 242° to 246° C.

EXAMPLE 2

30.9 grams (0.1 mole) of the 2,2-diethyl-5,5-dimethyl-4-thiazolidinyl phosphonic acid diethyl ester obtained according to Example A2 were treated successively with 40 ml of 12N aqueous hydrochloric acid and 210 ml of water. The mixture was subjected to a steam distillation for 23 hours.

Thereby there were distilled 4000 ml. The remaining reaction mixture was brought to dryness in a rotary evaporator. The residue was dissolved with heating in 40 ml of 6N aqueous hydrochloric acid, the solution treated with 400 ml of ethanol and adjusted to pH 5 by addition of trimethylamine. Thereby there separated out the 1-amino-2-mercapto-2-methylpropyl phosphonic acid in the form of colorless crystals. It was filtered under suction, washed successively with ethanol and diethyl ether and subsequently suction dried. The yield was 16.1 grams, corresponding to 87%. The melting point of the material was 243° to 246° C.

EXAMPLE 3

4.2 grams of the 2,2,5,5-tetramethyl-4-thiazolidinyl phosphonic acid diethyl ester obtained according to Example A5 was held in 20 ml of semi-concentrated aqueous hydrochloric acid for 5 hours under reflux at the boiling point. The mixture was evaporated to dryness, the residue dissolved in 10 ml of water with heating and the solution clarified with activated carbon. In the cooling there separated out crystalline 1-amino-2-mercapto-2-methylpropyl phosphonic acid. The material was filtered off and washed with 3 ml of water. The filtrate was adjusted to pH 3 by the addition of triethylamine and then treated with an equal volume of ethanol. Thereby there separated out a further amount of 1-amino-2-mercapto-2-methylpropyl phosphonic acid. The yield altogether was 2.5 grams, corresponding to 89%. The melting point of the material was 249° to 251° C.

EXAMPLE 4

There were used the reaction mixture directly as produced according to Example A5 as it was present before the distillation and it was treated with 790 ml of semi-concentrated aqueous hydrochloric acid. The mixture was held under reflux at the boiling temperature for 5 hours, then subjected to a steam distillation for 2 hours and finally brought to dryness. The residue was dissolved in 345 ml of water, the solution clarified with acticated carbon, mixed with 345 ml of ethanol and adjusted to pH 3 by addition of triethylamine. The 1-amino-2-mercapto-2-methylpropyl phosphonic acid separated thereby, was filtered off, washed with ethanol and diethyl ether and finally dried at 80° C. and 25 mbar. The yield was 85.3 grams, corresponding to 89%. The melting point of the material was 249° to 251° C.

EXAMPLE 5

2.93 grams (0.01 mole) of the 2-isopropyl-5,5-dimethyl-4-thiazolidinyl methyl phosphinic acid isobutyl ester obtained according to Example A6 was suspended in 50 ml of semi-concentrated aqueous hydrochloric acid. The mixture was held for 2.5 hours under reflux at the boiling temperature, then subjected for 4 hours to a steam distillation and finally brought to dryness in a rotary evaporator. The residue was dissolved in 30 ml of water. The solution was mixed with 100 ml of ethanol and adjusted to pH 5.1 by addition of triethylamine. Thereby there separated out 1-amino-2-mercapto-2-methylpropyl methylphosphinic acid in the form of colorless crystals. The material was filtered off, washed with a mixture of propanol-2 and methyl tert. butyl ether and finally dried. The yield was 1.72 grams corresponding to 94%. The melting point was 221° C.

What is claimed is:

1. A process for the production of 1-amino-2-mercapto-2-methylpropyl phosphonic acid or a 1-amino-2-mercapto-2-methylpropyl alkylphosphinic acid of the formula

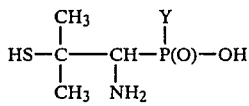

where Y is a hydroxy group or is $R_1$, where $R_1$ is an alkyl group from a thiazoline-(3) compound and a phosphorus compound comprising reacting a thiazoline-(3) of the formula

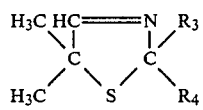

where $R_3$ and $R_4$ are each hydrogen, an alkyl group or are joined together with the adjacent carbon atom of the thiazoline-(3) ring to form a closed ring with an ester of the formula

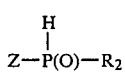

where $R_2$ is an alkoxy group and Z is $R_1$ or $R_2$ and hydrolytically splitting the ester formed of the formula

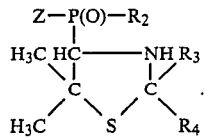

2. A process according to claim 1 wherein $R_1$ is alkyl of 1 to 12 carbon atoms, $R_2$ is an alkoxy group of 1 to 12 carbon atoms, $R_3$ and $R_4$ are hydrogen, alkyl of 1 to 3 carbon atoms or are joined together with the adjacent carbon atoms of the thiazoline-(3) ring to form a closed alkylene ring with 5 to 8 carbon atoms.

3. A process according to claim 2 where Y is a hydroxy group.

4. A process according to claim 3 where $R_3$ and $R_4$ are hydrogen or an alkyl group of 1 to 3 carbon atoms, Z is $R_2$ and $R_2$ is alkoxy of 1 to 4 carbon atoms.

5. A process according to claim 3 where $R_3$ and $R_4$ are joined together with the adjacent carbon atom of the thiazoline-(3) to form a carbon ring of 5 to 6 members, Z is $R_2$ and $R_2$ is alkoxy of 1 to 4 carbon atoms.

6. A process according to claim 2 where Y is $R_1$ and $R_1$ is alkyl of 1 to 4 carbon atoms.

7. A process according to claim 6 where $R_3$ and $R_4$ are hydrogen or an alkyl group of 1 to 3 carbon atoms and $R_2$ is alkoxy of 1 to 4 carbon atoms.

8. A process according to claim 6 where $R_3$ and $R_4$ are joined together with the adjacent carbon atom of the thiazoline-(3) to form a carbon ring of 5 to 6 members and $R_2$ is alkoxy of 1 to 4 carbon atoms.

9. A process according to claim 1 where Y is $R_1$.

10. An ester of a thiazolidinyl phosphonic acid or a thiazolidinyl alkylphosphinic acid of the formula

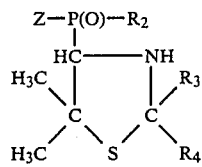

where Z is $R_1$ and $R_1$ is alkyl and $R_2$ is alkoxy and $R_3$ and $R_4$ are hydrogen, alkyl of 1 to 12 carbon atoms or are joined together with the adjacent carbon atom of the thiazoline-(3) ring to form a closed ring.

11. A ester of a thiazolidinyl phosphonic acid or a thiazolidinyl alkylphosphinic acid of the formula:

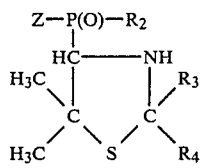

where Z is $R_1$ or $R_2$ and $R_1$ is alkyl and $R_2$ is alkoxy and $R_3$ and $R_4$ are joined together with the adjacent carbon atoms of the thiazoline-(3) ring to form a closed ring.

12. An ester according to claim 10 where Z is alkyl of 1 to 4 carbon atoms and $R_2$ is alkoxy of 1 to 4 carbon atoms.

13. An ester according to claim 12 where Z is methyl.

14. An ester according to claim 13 where $R_2$ is isobutoxy, $R_3$ is hydrogen and $R_4$ is isopropyl.

15. An ester according to claim 13 where $R_2$ is isobutoxy and $R_3$ and $R_4$ together are pentamethylene.

16. An ester according to claim 11 where Z is $R_2$ and $R_2$ is alkoxy of 1 to 4 carbon atoms.

17. An ester according to claim 10 where $R_2$ is ethoxy and $R_3$ and $R_4$ together are tetramethylene.

18. An ester according to claim 10 where $R_2$ is ethoxy and $R_3$ and $R_4$ together are pentamethylene.

* * * * *